United States Patent
Takenaka et al.

(10) Patent No.: US 10,349,914 B2
(45) Date of Patent: Jul. 16, 2019

(54) RADIATION IMAGING APPARATUS AND METHOD OF CONTROLLING THE SAME

(71) Applicant: CANON KABUSHIKI KAISHA, Tokyo (JP)

(72) Inventors: Katsuro Takenaka, Honjo (JP); Tomoyuki Yagi, Chofu (JP); Takuya Ryu, Kokubunji (JP); Shinichi Takeda, Kawasaki (JP); Hideyuki Okada, Honjo (JP); Eriko Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/757,693

(22) PCT Filed: Oct. 21, 2016

(86) PCT No.: PCT/JP2016/081283
§ 371 (c)(1),
(2) Date: Mar. 6, 2018

(87) PCT Pub. No.: WO2017/094393
PCT Pub. Date: Jun. 8, 2017

(65) Prior Publication Data
US 2019/0038250 A1 Feb. 7, 2019

(30) Foreign Application Priority Data
Dec. 1, 2015 (JP) .................................. 2015-235106

(51) Int. Cl.
*G01T 1/00* (2006.01)
*A61B 6/00* (2006.01)
(Continued)

(52) U.S. Cl.
CPC ............. *A61B 6/542* (2013.01); *A61B 6/4233* (2013.01); *G01T 1/208* (2013.01); *G01T 1/2018* (2013.01);
(Continued)

(58) Field of Classification Search
CPC ....... G01T 1/20; G01T 1/2006; G01T 1/2008; G01T 1/201; G01T 1/2012; G01T 1/2018; G01T 1/202; G01T 1/203; G01T 1/204
See application file for complete search history.

(56) References Cited

U.S. PATENT DOCUMENTS 7,256,404 B2   8/2007  Inoue et al.
7,342,221 B2   3/2008  Takenaka et al.
(Continued)

FOREIGN PATENT DOCUMENTS

JP   H07-201490   8/1995
JP   2010-075556  4/2010

OTHER PUBLICATIONS

U.S. Appl. No. 15/767,299, Toshio Kameshima, filed Nov. 8, 2016.
(Continued)

*Primary Examiner* — David P Porta
*Assistant Examiner* — Mamadou Faye
(74) *Attorney, Agent, or Firm* — Venable LLP

(57) ABSTRACT

A radiation imaging apparatus, including a plurality of pixels, a plurality of column lines and a processor, the plurality of pixels including first pixels and second pixels configured to generate signals of different values by receiving radiation rays of equal irradiation rates, and the plurality of pixels being arrayed such that their numbers are different between a first column and a second column of the plurality of columns, wherein the processor, after radiation irradiation is started, obtains a first signal of the first column and a second signal of the second column while maintaining each (Continued)

pixel to an OFF state and performs AEC based on the first and second signals.

17 Claims, 11 Drawing Sheets

(51) Int. Cl.
  *H04N 5/32* (2006.01)
  *G01T 1/20* (2006.01)
  *G01T 1/208* (2006.01)
  *H01L 27/146* (2006.01)
  *H04N 5/355* (2011.01)
  *H04N 5/361* (2011.01)

(52) U.S. Cl.
  CPC .. *H01L 27/14612* (2013.01); *H01L 27/14623* (2013.01); *H01L 27/14663* (2013.01); *H04N 5/32* (2013.01); *H04N 5/35563* (2013.01); *H04N 5/361* (2013.01); *H01L 27/14636* (2013.01)

(56) References Cited

U.S. PATENT DOCUMENTS

| | | |
|---|---|---|
| 7,343,000 B2 | 3/2008 | Kameshima et al. |
| 7,381,963 B2 | 6/2008 | Endo et al. |
| 7,386,089 B2 | 6/2008 | Endo et al. |
| 7,391,029 B2 | 6/2008 | Takeda et al. |
| 7,403,594 B2 | 7/2008 | Endo et al. |
| 7,421,063 B2 | 9/2008 | Takenaka et al. |
| 7,442,939 B2 | 10/2008 | Yagi et al. |
| 7,470,911 B2 | 12/2008 | Yagi et al. |
| 7,476,027 B2 | 1/2009 | Takenaka et al. |
| 7,514,663 B2 | 4/2009 | Yagi et al. |
| 7,514,686 B2 | 4/2009 | Ogawa et al. |
| 7,532,706 B2 | 5/2009 | Kameshima et al. |
| 7,541,591 B2 | 6/2009 | Endo et al. |
| 7,573,038 B2 | 8/2009 | Yokoyama et al. |
| 7,595,493 B2 | 9/2009 | Okada et al. |
| 7,613,277 B2 | 11/2009 | Takenaka et al. |
| 7,683,337 B2 | 3/2010 | Takenaka et al. |
| 7,714,294 B2 | 5/2010 | Sawada et al. |
| 7,718,973 B2 | 5/2010 | Endo et al. |
| 7,723,693 B2 | 5/2010 | Okada et al. |
| 7,724,874 B2 | 5/2010 | Kameshima et al. |
| 7,732,776 B2 | 6/2010 | Takenaka et al. |
| 7,750,309 B2 | 7/2010 | Endo et al. |
| 7,777,167 B2 | 8/2010 | Takeda et al. |
| 7,786,448 B2 | 8/2010 | Endo et al. |
| 7,791,034 B2 | 9/2010 | Kameshima et al. |
| 7,791,035 B2 | 9/2010 | Yokoyama et al. |
| 7,847,263 B2 | 12/2010 | Yagi et al. |
| 7,869,568 B2 | 1/2011 | Yokoyama et al. |
| 7,872,218 B2 | 1/2011 | Endo et al. |
| 7,880,145 B2 | 2/2011 | Yagi et al. |
| 7,952,058 B2 | 5/2011 | Nomura et al. |
| 7,965,817 B2 | 6/2011 | Kameshima et al. |
| 7,994,481 B2 | 8/2011 | Yagi et al. |
| 8,093,562 B2 | 1/2012 | Yokoyama et al. |
| 8,107,588 B2 | 1/2012 | Kameshima et al. |
| 8,115,177 B2 | 2/2012 | Takeda et al. |
| 8,167,486 B2 | 5/2012 | Takenaka et al. |
| 8,222,611 B2 | 7/2012 | Yagi et al. |
| 8,247,779 B2 | 8/2012 | Kameshima et al. |
| 8,304,735 B2 | 11/2012 | Inoue et al. |
| 8,440,975 B2 | 5/2013 | Inoue et al. |
| 8,576,294 B2 | 11/2013 | Kameshima et al. |
| 8,653,463 B2 | 2/2014 | Sawada et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 9,048,154 B2 | 6/2015 | Takenaka et al. |
| 9,081,104 B2 | 7/2015 | Sawada et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,354,333 B2 | 5/2016 | Inoue et al. |
| 9,366,767 B2 | 6/2016 | Inoue et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,737,271 B2 | 8/2017 | Iwashita et al. |
| 9,812,474 B2 | 11/2017 | Yagi et al. |
| 9,885,790 B2 | 2/2018 | Okada et al. |
| 2010/0148080 A1 | 6/2010 | Endo et al. |
| 2011/0317054 A1 | 12/2011 | Kameshima et al. |
| 2013/0121464 A1 | 5/2013 | Tajima |
| 2013/0187054 A1 | 7/2013 | Ishii et al. |
| 2013/0221198 A1 | 8/2013 | Sawada et al. |
| 2013/0223592 A1* | 8/2013 | Sato ............... A61B 6/4233 378/62 |
| 2014/0034836 A1 | 2/2014 | Takei et al. |
| 2014/0111674 A1* | 4/2014 | Iwasaki ............ H04N 9/045 348/294 |
| 2014/0112448 A1 | 4/2014 | Takenaka et al. |
| 2014/0239186 A1 | 8/2014 | Sato et al. |
| 2014/0361189 A1 | 12/2014 | Kameshima et al. |
| 2016/0084969 A1 | 3/2016 | Sato et al. |
| 2016/0178764 A1 | 6/2016 | Ryu et al. |
| 2016/0270755 A1 | 9/2016 | Takenaka et al. |
| 2017/0285189 A1 | 10/2017 | Ryu et al. |
| 2018/0063933 A1 | 3/2018 | Okada et al. |
| 2018/0070906 A1 | 3/2018 | Terui et al. |

OTHER PUBLICATIONS

U.S. Appl. No. 15/561,122, Eriko Sato, filed Sep. 25, 2017.
U.S. Appl. No. 15/564,946, Kosuke Terui, filed Oct. 6, 2017.
U.S. Appl. No. 15/791,566, Atsushi Iwashita, filed Oct. 24, 2017.
U.S. Appl. No. 15/877,694, Hideyuki Okada, filed Jan. 23, 2018.

* cited by examiner

F I G. 2
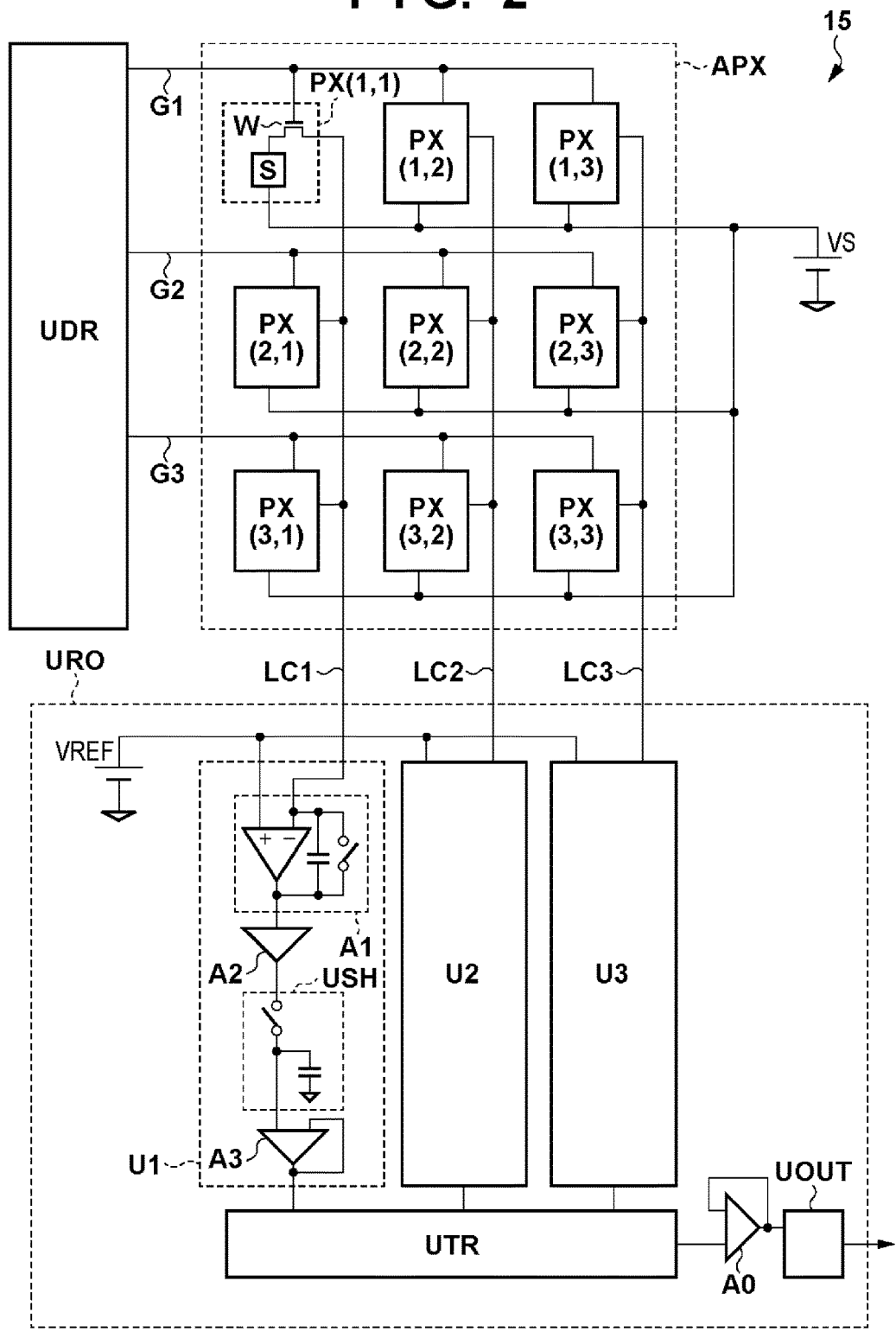

RADIATION IMAGING APPARATUS AND METHOD OF CONTROLLING THE SAME

TECHNICAL FIELD

The present invention relates to a radiation imaging apparatus and a method of controlling the same.

BACKGROUND ART

A radiation imaging apparatus includes, for example, a pixel array in which a plurality of pixels are arrayed to form a plurality of rows and a plurality of columns, and a readout unit for reading out a pixel signal from each pixel. In the pixel array, for example, a plurality of column lines respectively corresponding to the plurality of columns are arranged, and pixels on each column are connected to a corresponding column line. For example, each pixel includes a detecting element for detecting radiation, and a switch for connecting the detecting element and the corresponding column line. If the switch is turned on, a signal corresponding to an irradiation amount is transferred from the detecting element to the column line.

Some radiation imaging apparatuses monitor signals from pixels after radiation irradiation for the pixel array starts, and generate a control signal to end the radiation irradiation based on the monitoring result. This control is also called Auto Exposure Control (AEC). Japanese Patent Laid-Open No. 7-201490 describes a technique of performing AEC by reading out signals from some pixels in a predetermined cycle after the start of radiation irradiation. In addition, Japanese Patent Laid-Open No. 2010-75556 describes a technique of performing AEC by maintaining the switches of pixels on a given row in an ON state and monitoring the signals of the pixels after the start of radiation irradiation.

Even if the switch of a pixel is kept in an OFF state during radiation irradiation, a potential change of the pixel caused by emitted radiation (more specifically, a potential change caused by detection of radiation by the detecting element of the pixel) may propagate to the corresponding column line. Propagation of the potential change to the column line is caused by capacitance coupling between the pixel and the column line, which will be referred to as "crosstalk" hereinafter in this specification.

In the methods described in Japanese Patent Laid-Open Nos. 7-201490 and 2010-75556, a signal read out via a column line includes a signal component from a pixel as a readout target and crosstalk components from the remaining pixels as non-readout targets. Especially, the crosstalk components have a larger value as the number of pixels increases, thereby decreasing the S/N ratio. This may decrease the accuracy of AEC.

SUMMARY OF INVENTION

The present invention provides a technique advantageous in increasing the accuracy of AEC of a radiation imaging apparatus.

One of the aspects of the present invention provides a radiation imaging apparatus including a plurality of pixels which are arrayed to form a plurality of rows and a plurality of columns and each of which includes a detecting element configured to detect radiation and a switch connected to the detecting element, a plurality of column lines respectively corresponding to the plurality of columns and each connected to respective pixels on the corresponding column, and a processor, wherein the plurality of pixels include first pixels and second pixels configured to generate signals of different values by receiving radiation rays of equal irradiation rates, the first pixels and the second pixels are arranged so that the numbers of the first pixels and the second pixels are different between a first column and a second column of the plurality of columns, and the processor performs a first operation of acquiring, as a first signal, a signal of a column line corresponding to the first column and acquiring, as a second signal, a signal of a column line corresponding to the second column while the switch of each pixel is maintained in an OFF state after radiation irradiation for the plurality of pixels starts, a second operation of calculating, based on a discrepancy between the first signal and the second signal, an irradiation amount after the radiation irradiation starts, and a third operation of outputting a signal to end the radiation irradiation in response to a fact that the calculated irradiation amount has reached a reference value.

Further features of the present invention will become apparent from the following description of exemplary embodiments with reference to the attached drawings.

BRIEF DESCRIPTION OF DRAWINGS

FIG. 2 is a circuit diagram for explaining an example of the arrangement of an imaging unit;

DESCRIPTION OF EMBODIMENTS

Figure 1:
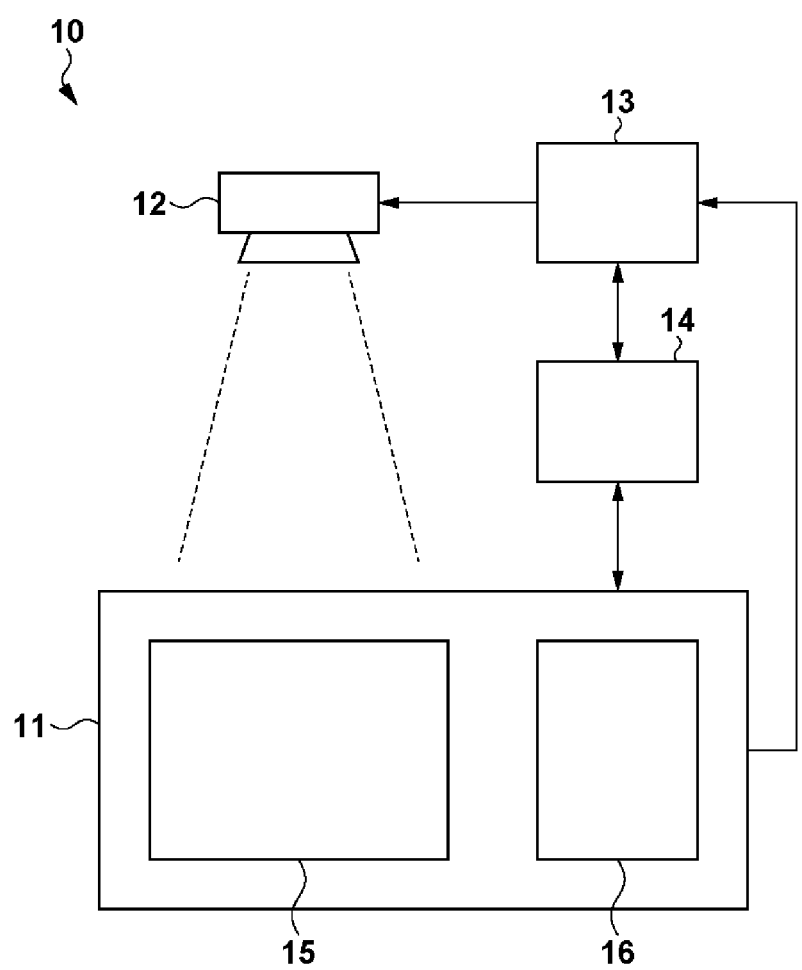
FIG. 1 is a view for explaining an example of the system configuration of a radiation imaging apparatus.

A preferred embodiment of the present invention will be described below with reference to the accompanying drawings. Note that the respective drawings are merely drawn for the purpose of explaining structures and arrangements, and the scales of respective members shown in the drawings do not always reflect actual scales. Throughout the drawings, the same reference numerals denote the same members or components, and a repetitive description thereof will be omitted.

FIG. 1 shows an example of the system configuration of an imaging system 10 (to be also referred to as a radiation inspection apparatus, a radiation diagnostic apparatus, or the like) for performing radiation imaging. The imaging system 10 includes, for example, a radiation imaging apparatus 11, a radiation source 12, a radiation control unit 13, and a controller 14. The radiation imaging apparatus 11 includes an imaging unit 15 and a processor 16. The radiation source 12 generates radiation (for example, X-rays, α-rays, β-rays, or the like) in response to a driving signal from the radiation control unit 13. The radiation passes through an object (a patient or the like) (not shown), and is detected by the imaging unit 15. The imaging unit 15 generates image data in correspondence with an irradiation amount. The processor 16 performs data processing such as correction processing for the image data from the imaging unit 15.

The controller 14 controls the overall operation of the imaging system 10 by exchanging signals, data, commands, and the like with, for example, the radiation imaging apparatus 11, the respective units of it, and the radiation control unit 13. For example, the radiation control unit 13 controls the radiation source 12 by receiving, from the controller 14, a command to start or end radiation irradiation. Note that some or all of the functions of the radiation control unit 13 may be included in the controller 14.

The controller 14 is connected to a terminal (not shown) used by the user to input imaging conditions, and performs the above-described control operation based on the input imaging conditions. Furthermore, the controller 14 is connected to a display unit (not shown) such as a liquid crystal display, and can output, to the display unit, the image data obtained by the radiation imaging apparatus 11, and display a radiation image on the display unit.

Although details will be described later, the radiation imaging apparatus 11 causes the processor 16 to calculate an irradiation amount after the start of radiation irradiation. If the irradiation amount exceeds a reference value, the radiation imaging apparatus 11 causes the processor 16 to request, for example, the controller 14 or the radiation control unit 13 to end the radiation irradiation (Auto Exposure Control (AEC)). The irradiation amount corresponds to the time integration of an irradiation rate (radiation intensity).

An example of the arrangement of the imaging system 10 is not limited to this, as a matter of course. The functions of some of the units of the imaging system 10 may be included in other units, and a unit having another function may be added. For example, in the radiation imaging apparatus 11, some of the functions of the imaging unit 15 may be implemented by the processor 16 and vice versa. For example, the processor 16 and the controller 14 are separately shown in FIG. 1. However, some or all of the functions of the processor 16 and the controller 14 may be implemented by a single unit. The processor 16 may be, for example, a PLD (Programmable Logic Device) such as an integrated circuit or device (for example, an FPGA (Field Programmable Gate Array) capable of programming the respective functions described in this specification, or an ASIC (Application Specific Integrated Circuit) for implementing the respective functions. Alternatively, the respective functions may be implemented by software in a personal computer or the like storing predetermined programs. The same applies to the controller 14.

FIG. 2 shows an example of the arrangement of the imaging unit 15 in the radiation imaging apparatus 11. The imaging unit 15 includes, for example, a pixel array APX in which a plurality of pixels PX are arrayed, a driving unit UDR for driving the respective pixels PX, and a readout unit URO for reading out pixel signals from the respective pixels PX.

The plurality of pixels PX are arrayed to form a plurality of rows and a plurality of columns. For the sake of descriptive simplicity, the pixel array APX of 3 rows×3 columns will be exemplified. In fact, for example, a 17-inch pixel array APX includes about 3,000 rows×3,000 columns. Note that in FIG. 2, the pixel PX on the mth row and the nth column is represented by "PX(m, n)" (for example, a pixel PX(1, 1) is located on the first row and the first column in the pixel array APX).

The driving unit UDR includes, for example, a shift register, and sequentially drives the plurality of pixels PX for each row by sequentially selecting one (or two or more) of the plurality of rows. More specifically, the driving unit UDR supplies a driving signal to each of the corresponding pixels PX via one of signal lines G1 to G3 corresponding to each row. Upon receiving the driving signal, each of the pixels PX outputs a pixel signal to a corresponding one (to be also referred to as a "corresponding column line" hereinafter) of column lines LC1 to LC3. Note that in this specification, if the column lines LC1 to LC3 are not discriminated, they will be simply referred to as "column signal lines LC" hereinafter.

Each pixel PX includes a switch W and a detecting element S for detecting radiation. Although FIG. 2 shows only the detecting element S and the switch W for the pixel PX(1, 1), the remaining pixels PX also have the same arrangement. In this embodiment, a MIS sensor is used as the detecting element S. However, a PIN sensor or another known photoelectric conversion element may be used. Note that the "detecting element" may be expressed as a "sensor", a "sensor element", or the like. Accordingly, the "pixel array" may be expressed as a "sensor array" or the like. Although a thin-film transistor is used as the switch W in this embodiment, another known switch element may be used. In each pixel PX, one terminal of the detecting element S is connected to the corresponding column line LC via the switch W, and the other terminal of the detecting element S can be connected to a power supply line through which a power supply voltage VS propagates.

Figure 3:
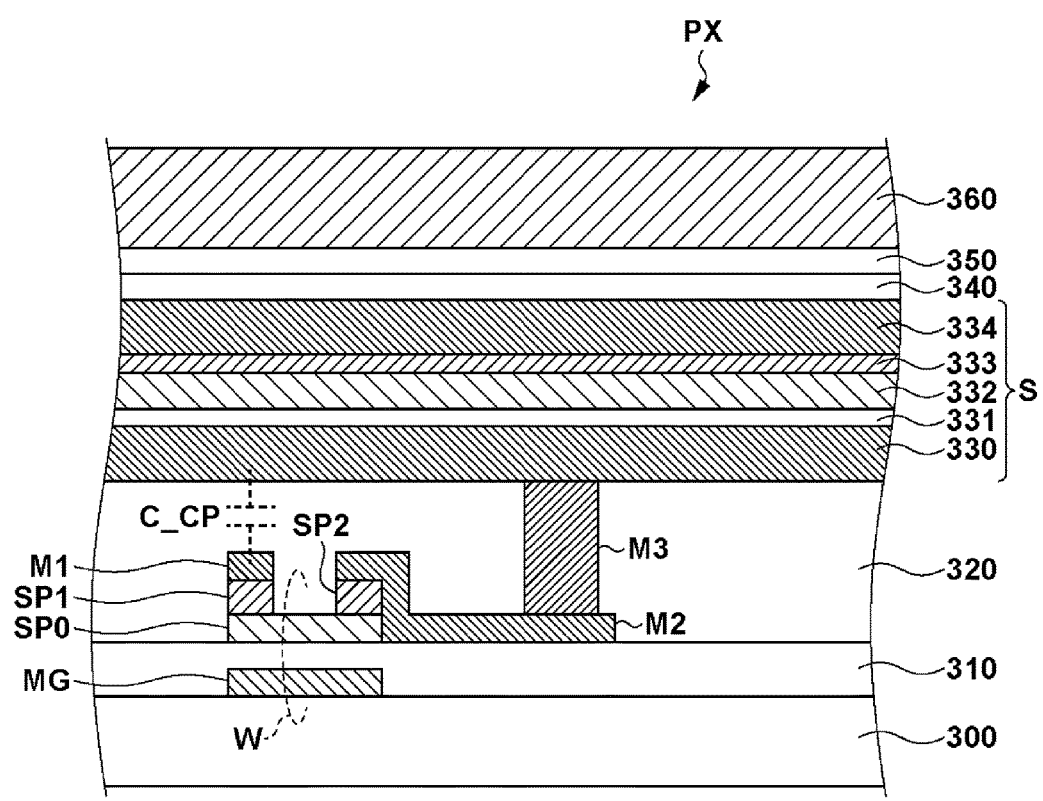
FIG. 3 is a sectional view for explaining an example of the structure of a unit pixel.

FIG. 3 is a schematic view for explaining an example of the structure of the unit pixel PX. The switch W as a thin-film transistor is arranged on, for example, an insulation substrate 300 (a glass substrate or the like), and is connected to the detecting element S arranged on an insulation layer 320 on the substrate 300. An electrode MG arranged on the upper surface of the substrate 300 serves as the gate electrode of the thin-film transistor. A semiconductor portion SP0 is arranged on an insulation film 310, part of which forms a gate insulation film, on the gate electrode MG, and forms the channel of the thin-film transistor. A semiconductor portion SP1 doped with, for example, an n-type impurity is arranged on one end of the semiconductor portion SP0, forms the source of the thin-film transistor, and is connected to an electrode M1 as part of the column line LC. A semiconductor portion SP2 doped with the same impurity is arranged on the other end of the semiconductor portion SP0, forms the drain of the thin-film transistor, and is connected to the detecting element S via an electrode M2 and a plug M3. Note that the semiconductor portions SP0 to SP2 are made of, for example, amorphous silicon or the like.

The detecting element S includes, for example, layers 330 to 334 sequentially arranged from bottom to top in FIG. 3. The layer 330 serves as a conductive layer forming the lower electrode of the detecting element S, and is in contact with the plug M3. The layer 331 serves as an insulation layer. The layer 332 serves as a semiconductor layer. The layer 333 serves as a high impurity concentration semiconductor layer doped with, for example, an n-type impurity. The layer 334 serves as a conductive layer forming the upper electrode of the detecting element S, and can be made of a transparent conductive material (for example, an indium tin oxide (ITO) or the like).

A scintillator 360 for converting radiation into light can be arranged on an adhesive layer 350 on a protection layer 340 on the detecting element S. A gadolinium-based material such as gadolinium oxide sulfur (GOS) or a material such as cesium iodide (CsI) can be used for the scintillator 360. In this embodiment, the detecting element S detects the light (scintillation light) converted by the scintillator 360 from the radiation. This is equivalent to detection of the radiation. The scintillator 360 and the detecting element S may be collectively referred to as a conversion unit or conversion element for converting radiation into an electrical signal.

Note that a method (indirect conversion type) of converting radiation into light and then converting the light into an electrical signal has been exemplified. In another example, a method (direct conversion type) of directly converting radiation into an electrical signal may be adopted. In the case of the direct conversion type, for example, a material such as amorphous selenium, gallium arsenide, gallium phosphide, lead iodide, mercury iodide, CdTe, or CdZnTe can be used for the detecting element S.

The electrode M1 forming part of the column line LC can substantially overlap the detecting element S (or a region corresponding to one pixel PX) in a planar view (a planar view with respect to the upper surface of the substrate 300 or a surface parallel to it). This can increase the size of the detecting element S and/or the effective region of the pixel PX in a planar view. On the other hand, although details will be described later, a capacitance component C_CP is formed between the electrode M1 and the conductive layer 330 (or each of the plug M3, the electrode M2, and the semiconductor portion SP2, which has a potential equal to that of the conductive layer 330) forming the lower electrode, as indicated by a broken line in FIG. 3. Therefore, a potential change of the conductive layer 330 is undesirably transferred to the electrode M1 by capacitance coupling by the capacitance component C_CP even if the switch W is OFF (non-conductive).

Referring back to FIG. 2, in each pixel PX, a signal corresponding to the irradiation amount detected by the detecting element S is output to the corresponding column line LC by turning on the switch W (rendering the switch W conductive). The readout unit URO reads out, for each column, the pixel signal output via the column line LC on each column.

The readout unit URO includes, for example, units U1 to U3 respectively arranged on the first to third columns, a horizontal transfer unit UTR, a buffer circuit A0, and an output unit UOUT. For example, the unit U1 can include an integration amplifier A1, a variable amplifier A2, a sample/hold circuit USH, and a buffer circuit A3. Note that a practical example of the arrangement of the unit U1 is shown, and the same applies to the remaining units U2 and U3.

The integration amplifier A1 includes, for example, an operational amplifier, a feedback capacitor arranged in a path between the inverting input terminal ("−" terminal in FIG. 2) of the operational amplifier and the output terminal of the operational amplifier, and a reset switch arranged in parallel to the feedback capacitor. A reference voltage VREF is supplied to the non-inverting input terminal ("+" terminal in FIG. 2) of the operational amplifier. While the reset switch is OFF, the pixel signal (more specifically, a potential fluctuation in the column line LC) output from the pixel PX via the column line LC is amplified by the integration amplifier A1. When the reset switch is turned on, the integration amplifier A1 is reset or initialized.

The pixel signal amplified by the integration amplifier A1 is further amplified by a predetermined gain by the variable amplifier A2, and sampled by the sample/hold circuit USH. The sample/hold circuit USH includes, for example, a sampling switch and a sampling capacitor connected to it. When the sampling switch is turned on, the sampling capacitor is charged to have a voltage corresponding to the pixel signal (sample). When the sampling switch is turned off, the sampling capacitor is made to hold the voltage, thereby fixing the voltage (hold). The sampled pixel signal is output to the horizontal transfer unit UTR via the buffer circuit A3.

The horizontal transfer unit UTR can include, for example, a multiplexer and a shift register (neither of which is shown), and sequentially, horizontally transfers the pixel signal read out for each column by sequentially selecting each column. The horizontally transferred pixel signal is output to the processor 16 via the buffer circuit A0 and the output unit UOUT. The output unit UOUT can include, for example, an analog-to-digital converter, and the thus readout pixel signal group can be supplied to the processor 16 as image data.

Note that in the above-described arrangement, a signal for controlling the reset switch, the sampling switch, and other elements (not shown) may be supplied from, for example, the processor 16. In another example, this signal may be supplied from another unit (for example, a timing adjustment circuit including a PLL (Phase Locked Loop), or the like) associated with the operation of the processor 16.

Examples of the arrangements of the imaging unit 15 and the pixel PX are not limited to those described in this embodiment, as a matter of course. Parts of the above-described examples of the arrangements may be changed, and other elements may be added.

Figure 4:
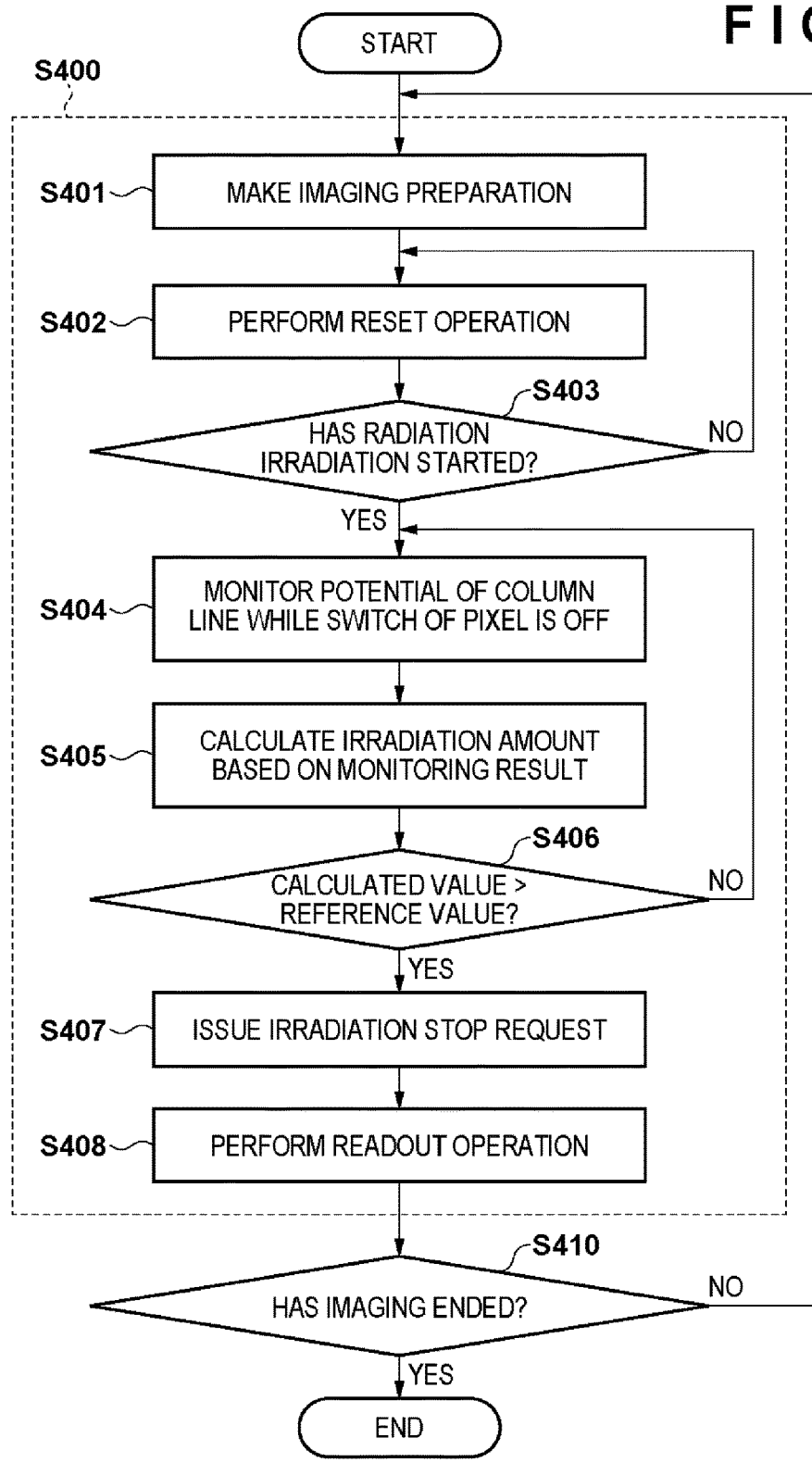
FIG. 4 is an operation flowchart illustrating radiation imaging.

FIG. 4 is an operation flowchart at the time of imaging of the radiation imaging apparatus 11. In step S400 (to be simply referred to as "S400" hereinafter) (the same applies to other steps), image data of one frame (image data corresponding to one radiation image) is acquired. After that, it is determined in S410 whether imaging has ended. If it is determined that imaging has ended, the flowchart ends; otherwise, the process returns to S400. For example, if image data of n frames are acquired where n represents an integer of 1 or more, the flowchart ends after S400 is performed n times.

S400 includes S401 to S408. In S401, imaging preparation is made based on imaging conditions input by the user and, for example, conditions and parameters necessary to perform radiation imaging are set in a corresponding unit. The settings include settings necessary to appropriately perform AEC in accordance with the imaging conditions such as a portion to be imaged and an irradiation amount.

In S402, a reset operation (to be referred to as a "reset operation RS" hereinafter) is performed. More specifically, each pixel PX of the pixel array APX is reset. The reset operation RS is performed by sequentially turning on the switches W of the pixels PX for each row. Note that the reset operation RS is similar to a readout operation RO (to be described later) except that the readout unit URO is in a sleep state (for example, a state in which the integration amplifier A1 has been reset).

In S403, it is determined whether radiation irradiation has started. If it is determined that radiation irradiation has started, the process advances to S404; otherwise, the process returns to S402. The determination processing in S403 is performed by a known determination method, and may be performed, for example, based on the amount of a current flowing to the power supply line of the power supply voltage VS, or by using a sensor separately provided for detecting the start of radiation irradiation. In another example, the determination processing may be performed using, for example, a synchronization signal in response to the pressing, by the user, of a switch for starting radiation irradiation.

In S402 and S403, the above-described reset operation RS is repeatedly performed (the respective pixels PX of the pixel array APX are periodically reset) until radiation irradiation starts.

In S404, the potential of the column line LC on each column is monitored. This monitoring processing is performed while the switch W of each pixel PX is maintained in the OFF state. That is, in S404, the detecting element S of each pixel PX and the corresponding column line LC are not connected by the switch W. However, as described with reference to FIG. 3, a potential change of the detecting element S propagates to the corresponding column line LC by capacitance coupling by the capacitance component C_CP. Propagation of the potential change to the column line LC is also called "crosstalk".

In S405, based on the monitoring result (that is, the potential of each column line LC) in S404, the irradiation amount after the start of radiation irradiation is calculated. This calculation processing is performed based on the component (crosstalk component) of a potential fluctuation in the column line LC caused by the crosstalk. This will be described below as a practical example with reference to FIGS. 5A and 5B.

Figure 5A:
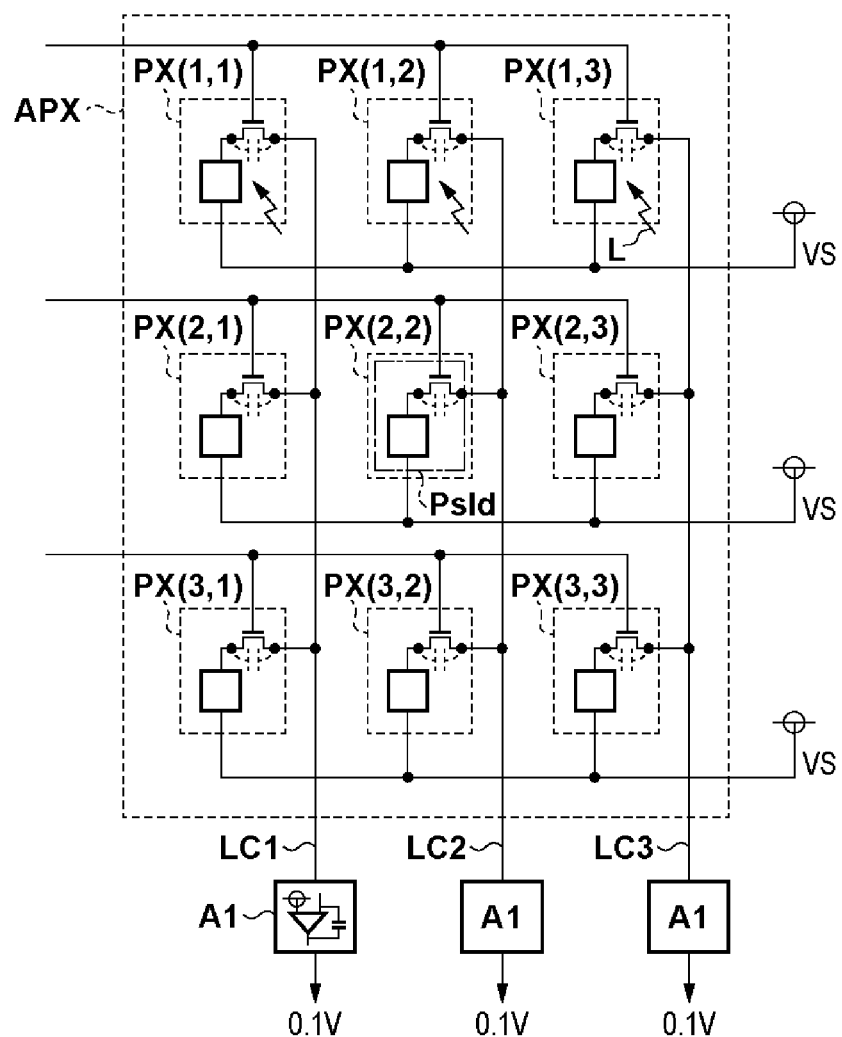
FIG. 5A is an equivalent circuit diagram for explaining an example of the arrangement of a pixel array.
Figure 5B:
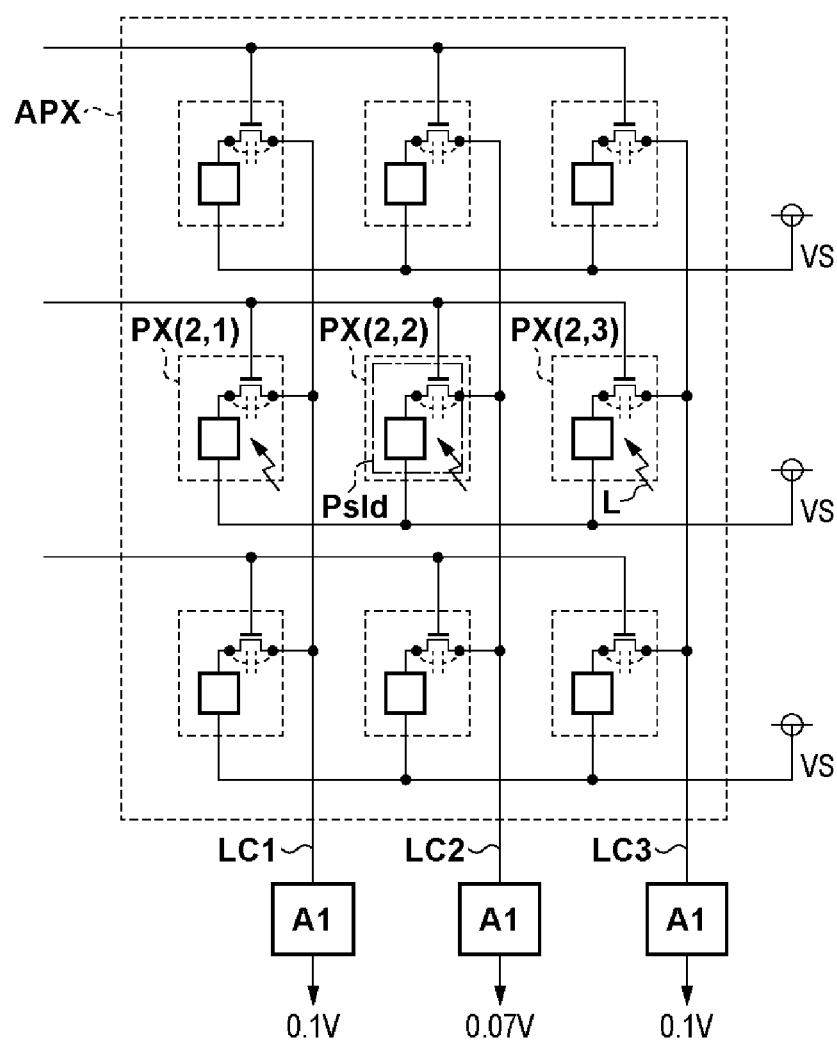
FIG. 5B is an equivalent circuit diagram for explaining an example of the arrangement of a pixel array.

FIGS. 5A and 5B each show part of the example of the arrangement of the imaging unit 15. In this embodiment, among pixels PX(1, 1) to PX(3, 3), the pixel PX(2, 2) and the remaining pixels PX(1, 1) and the like have different characteristics (for example, different arrangements or structures). In this embodiment, a light-shielding portion Psld is arranged on the pixel PX(2, 2). The light-shielding portion Psld is arranged, for example, between the scintillator 360 and the detecting element S so as to limit at least part of scintillation light. In this specification, a pixel (that is, the remaining pixels PX(1, 1) and the like) on which no light-shielding portion Psld is arranged may be referred to as a "first pixel PXa" hereinafter and a pixel (that is, the pixel PX(2, 2)) on which the light-shielding portion Psld is arranged may be referred to as a "second pixel PXb" hereinafter in order to discriminate between them.

In this embodiment, for example, even if the distribution of the scintillation light is substantially uniform on the pixels PX(1, 1) to PX(3, 3), the amount of incident light on the detecting element S of the pixel PX(2, 2) is small, as compared with the remaining pixels PX(1, 1) and the like. Therefore, a potential fluctuation at the pixel PX(2, 2) is different from those at the remaining pixels PX(1, 1) and the like.

For example, in the example of FIG. 5A, when light beams L of almost equal light amounts enter the pixels PX(1, 1) to PX(1, 3) on the first row, the outputs of the integration amplifiers A1 on the respective columns are almost equal to each other. To the contrary, in the example of FIG. 5B, when the light beams L of almost equal light amounts enter the pixels PX(2, 1) to PX(2, 3) on the second row, the output of the integration amplifier A1 on the second column is different from that of the integration amplifier A1 on the first (or third) column.

For example, assume that a source-drain capacitance in the OFF state of the switch W is 0.1 pF, and the feedback capacitance of the integration amplifier A1 is 1 pF. Assume also that a potential fluctuation along with the incidence of the light beam L at each of the remaining pixels PX(1, 1) and the like (except for the pixel PX(2, 2)) is 1 V. On the other hand, assume that the light amount of the light beam L at the pixel PX(2, 2) is limited by 30% by the light-shielding portion Psld, as compared with the remaining pixels PX(1, 1) and the like, and a potential fluctuation along with the incidence of the light beam L at the pixel PX(2, 2) is 0.7 V. In this case, in the example of FIG. 5A, the outputs of the integration amplifiers A1 on the first to third columns are all 0.1 V. To the contrary, in the example of FIG. 5B, the output of the integration amplifier A1 on the second column is 0.07 V (the outputs on the first and third columns are 0.1 V). That is, in the example of the arrangement, there is a substantial difference between the outputs of the integration amplifiers A1 on two adjacent columns (adjacent columns). This difference can be a difference between crosstalk components on a given column and its adjacent column.

In S405 described above, the irradiation amount is calculated based on the difference between the crosstalk components on adjacent columns with reference to the potentials of the respective column lines LC. This calculation processing can be performed based on the numbers of pixels of two types on the respective columns, that is, the numbers of first pixels PXa such as the remaining pixels PX(1, 1) and the like and the numbers of second pixels PXb such as the pixel PX(2, 2) on the respective columns, and the difference between the two types of pixels. Note that the difference between the two types of pixels PXa and PXb can be acquired in advance by actual measurement or simulation analysis.

The two types of pixels PXa and PXb are configured to mix different crosstalk components into the corresponding column line LC when they receive radiation rays of equal irradiation rates. The difference between the two types of pixels PXa and PXb depends on whether the light-shielding portion Psld is arranged (that is, whether the light amount of scintillation light entering the detecting element S is different between the two types of pixels) in this embodiment, but may depend on another factor. For example, the two types of pixels PXa and PXb may be configured to have different sensitivities of the detecting elements S to the scintillation light. In another example, the two types of pixels PXa and PXb may be configured to have different electrical characteristics of the switches W (for example, different source-drain capacitances in the OFF state of the switches W, different source-drain leak current amounts, or the like). In another example, the two types of pixels PXa and PXb may be configured to have different circuit arrangements. In still another example, the scintillators 360 arranged on the two types of pixels PXa and PXb may be configured to generate light beams of different light amounts upon receiving radiation rays of almost equal irradiation rates.

Referring back to FIG. 4, it is determined in S406 whether the value calculated in S405 exceeds the reference value. If the calculated value obtained in S405 exceeds the reference value, the process advances to S407; otherwise, the process returns to S404. The calculated value is a value corresponding to the irradiation amount after the start of radiation irradiation. The reference value is a value corresponding to the allowable amount of the irradiation amount, which may be a fixed value or a variable value settable based on the imaging conditions and the like in the imaging preparation processing in S401.

In S407, a radiation irradiation stop request is issued. More specifically, a signal to end (stop or interrupt) radiation irradiation is output, thereby ending radiation irradiation. The irradiation stop request may be directly sent to the radiation control unit 13 or may be sent to the radiation control unit 13 via the controller 14.

That is, in S404 to S407 described above, a monitoring operation (to be referred to as a "monitoring operation MO" hereinafter) of monitoring the potential of each column line LC in a predetermined cycle is performed, and AEC is performed based on the result of the monitoring operation.

After that, in S408, a readout operation (to be referred to as the "readout operation RO" hereinafter) is performed. More specifically, pixel signals are read out from the respective pixels PX by sequentially turning on the switches W of the respective pixels PX for each row, thereby generating image data of one frame.

In this embodiment, since the light-shielding portion Psld is arranged on the pixel PX(2, 2), the pixel signal from the pixel PX(2, 2) includes a signal component smaller than that of the pixel signal from each of the remaining pixels PX(1, 1) and the like. Therefore, of the image data, a portion (that is, the pixel signal of the pixel PX(2, 2)) corresponding to the pixel PX(2, 2) may undergo, for example, correction processing by the processor 16. For example, this correction processing is executed by performing multiplication by a corresponding gain for each pixel signal of the pixel data so as to compensate for a loss of the signal component along with the limitation of the light amount by the light-shielding portion Psld. For example, a gain which can be used for signal processing for the pixel signal of the pixel PX(2, 2) is different from that which can be used for signal processing for the pixel signal of each of the remaining pixels PX(1, 1) and the like.

If the pixel PX(2, 2) is configured to limit a larger light amount by the light-shielding portion Psld, the difference between the crosstalk components on the adjacent columns can be increased, thereby improving the accuracy of AEC. On the other hand, by limiting a larger light amount by the light-shielding portion Psld, the pixel signal of the pixel PX(2, 2) loses the signal component more. In this case, when generating image data, the pixel signal from the adjacent pixel (for example, the pixel PX(1, 2), PX(3, 2), or the like) of the pixel PX(2, 2) may be used without using the pixel signal of the pixel PX(2, 2). That is, the pixel signal of the pixel PX(2, 2) may be complemented or replaced using the pixel signal of the adjacent pixel.

Figure 6:
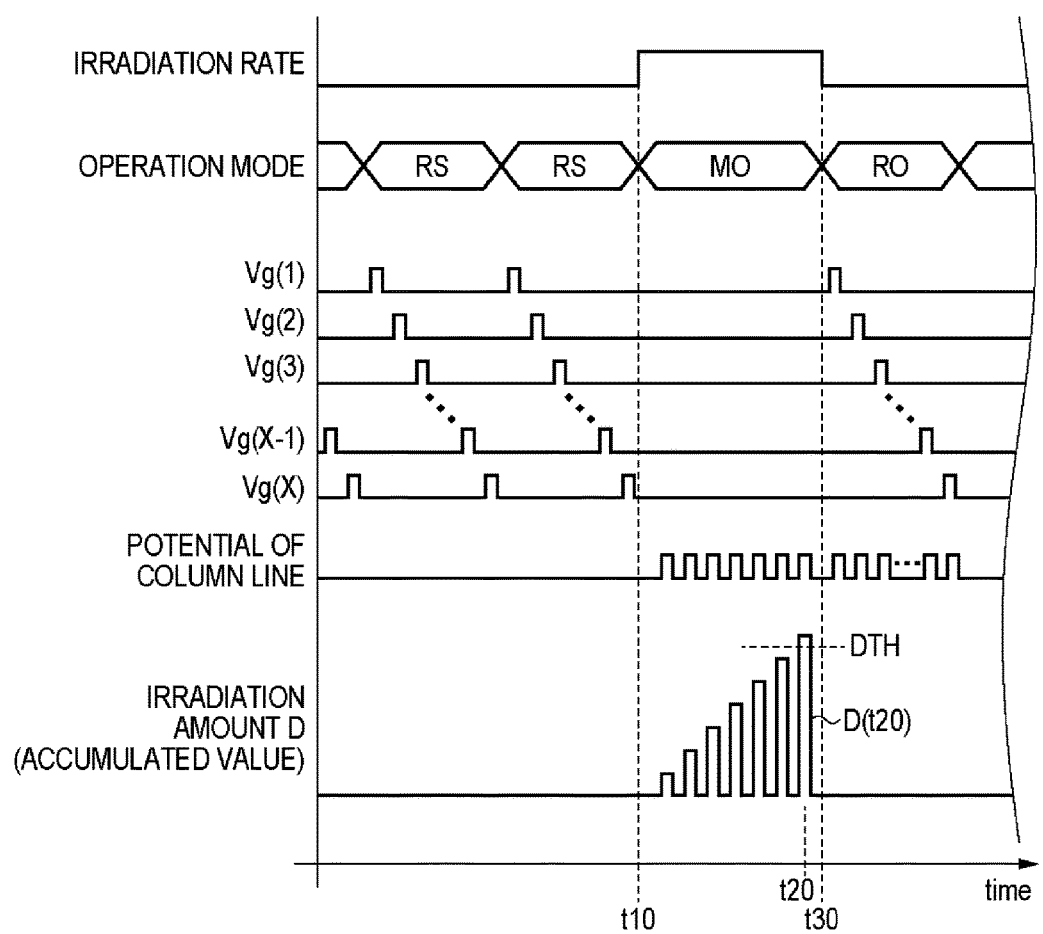
FIG. 6 is an operation timing chart showing radiation imaging.

FIG. 6 is an operation timing chart at the time of imaging of the radiation imaging apparatus 11. In FIG. 6, the abscissa represents the time, and the ordinate represents an irradiation rate (radiation intensity), the operation mode of the apparatus 11, potentials Vg(1) to Vg(X) of the signal lines corresponding to the respective rows, the potential of the column line, and an irradiation amount D. The irradiation amount D corresponds to the value calculated in S405 described above. The pixel array APX forms×rows and Y columns. In FIG. 6, Vg(1) to Vg(X) represent the potentials of the signal lines corresponding to the first to Xth rows. For example, if the potential Vg(1) is set at high level, the switches W of the pixels PX on the first row are turned on (the pixels PX on the first row are activated). If the potential Vg(1) is set at low level, the switches W of the pixels PX on the first row are turned off (the pixels PX on the first row is deactivated).

A period before time t10 is a period before the start of radiation irradiation, during which the reset operation RS is repeatedly performed. At time t10, radiation irradiation starts, and the monitoring operation MO is performed. The monitoring operation MO is performed by driving the readout unit URO in a predetermined cycle while the switch W of each pixel PX is OFF, and the readout unit URO reads out the crosstalk component mixed into each column line LC. More specifically, the potentials or signals of the column lines LC into which the crosstalk components are mixed are sequentially amplified and sampled by the unit U1 and the like arranged for the respective columns, and then output by the horizontal transfer unit UTR, the buffer circuit A0, and the output unit UOUT. The monitoring operation is performed in the predetermined cycle, as described above. This cycle can correspond to the cycle of sampling by the sample/hold circuit USH of the unit U1 or the like.

The irradiation amount D is obtained by accumulating the result of the monitoring operation performed in the predetermined cycle, and corresponds to the "calculated value" in S405. The irradiation amount D(t20) at time t20 becomes larger than a reference value DTH. In response to this, the radiation irradiation ends, and the monitoring operation MO ends. This time is indicated by time t30. After time t30, the readout operation RO starts.

In this embodiment, in the pixel array APX, the two types of pixels PXa and PXb which receive radiation rays of equal irradiation rates and generate different crosstalk components in the corresponding column lines LC. The two types of pixels PXa and PXb can be arranged so that the numbers of pixels PXa and PXb are different between adjacent columns. In the examples of FIGS. 5A and 5B, the pixels PX(1, 1) and the like except for the pixel PX(2, 2) correspond to the pixels PXa and the pixel PX(2, 2) corresponds to the pixel PXb.

With this arrangement, in the monitoring operation MO, a difference is generated between the voltages of the column lines LC on adjacent columns, that is, different monitoring results are obtained on adjacent columns. In the examples of FIGS. 5A and 5B, the output of the integration amplifier A1 corresponding to the crosstalk component of each of the remaining pixels PX(1, 1) and the like is 0.1 V, and the output of the integration amplifier A1 corresponding to the crosstalk component of the pixel PX(2, 2) is 0.07 V. Therefore, the difference between the outputs of the integration amplifiers A1 on the first (or third) column and the second column is 0.03 V. This difference can correspond to a difference obtained by replacing the pixel PX(2, 2) from one type of pixel PXa to the other type of pixel PXb. Consequently, based on the difference between the characteristics of the pixels PXa and PXb, the differences in numbers of pixels between adjacent columns, and the difference between the monitoring results on the adjacent columns (that is, the potential difference between the column lines LC on the adjacent columns), the irradiation amount can be calculated, thereby appropriately performing AEC.

When calculating the irradiation amount, the difference between the characteristics of the pixels PXa and PXb and the differences in numbers of pixels PXa and PXb between the adjacent columns are fixed, and thus a coefficient corresponding to the differences may be preset in the processor 16. That is, the processor 16 can appropriately calculate the irradiation amount using the coefficient based on the difference between the monitoring results on the adjacent columns (that is, the potential difference between the column lines LC on the adjacent columns). Note that in this embodiment, a case in which the number of pixels PXb on the first (or third) column is 0 has been exemplified. However, the numbers of pixels PXa and PXb need only be different between adjacent columns, and the number of pixels PXb need not be 0.

In general, the irradiation rates of the emitted radiation rays are considered to be almost equal to each other between adjacent columns of the pixel array APX. Thus, although a case in which AEC is performed based on the difference between the monitoring results on the adjacent columns has been exemplified in this embodiment, two columns as monitoring targets need not always be adjacent to each other. That is, although the accuracy of AEC becomes high by setting, as monitoring targets, two columns relatively close to each other (preferably, two adjacent columns), one or more other columns which are not monitoring targets may exist between the two columns as monitoring targets. In this case, the distance (upper limit value) between the two columns as monitoring targets may be defined by a value obtained by multiplying the size of the pixel array APX in the row direction by a predetermined ratio (for example, 1/10), or may be defined by an actual size (for example, 1 inch). Alternatively, the distance may be defined by the number of columns (for example, a distance corresponding to 100 columns) which are allowed to be arranged between the two columns.

The difference between the monitoring results on the two columns (preferably, the two adjacent columns) obtained by the monitoring operation MO corresponds to the potential difference between the column lines LC on the two columns, and can include the difference between the results of predetermined signal processes such as the outputs of the integration amplifier A1 and other circuits. In other words, AEC may be performed based on a calculation result obtained by predetermined calculation processing for the monitoring results of the two columns, and the potential difference between the column lines LC on the two columns or a signal value corresponding to it need not always be used intact. In another example, AEC may be performed based on the ratio between the potentials of the column lines LC on the two columns or a calculation result corresponding to it. That is, AEC need only be performed based on a discrepancy between the monitoring results of the two columns (the "discrepancy" can include an absolute or relative difference between the two columns, an amount corresponding to it, and a concept of another range).

In summary, in this embodiment, the pixels PXa and PXb are arranged so that the numbers of pixels PXa and PXb are different between two columns (preferably, two adjacent columns) in the pixel array APX. In this arrangement, AEC is performed by monitoring the potentials of the column lines LC on the two columns or signals corresponding to them while maintaining the switches W of the respective pixels PX in the OFF state. This can appropriately determine the timing at which radiation irradiation ends, thereby improving the accuracy of AEC.

Note that this embodiment has exemplified a case in which monitoring results are acquired in the same procedure as that for image data by causing the readout unit URO to read out the crosstalk components mixed into the column lines LC on two columns. However, a monitoring result acquisition method is not limited to that in this embodiment. For example, the readout unit URO is provided with a dedicated circuit unit for reading out, as a monitoring result, the crosstalk components mixed into the column lines LC on the two columns, the difference between them, or a signal corresponding to the difference, in addition to the unit U1 and the like for reading out image data.

When performing radiation imaging, the distribution of the irradiation rate of radiation to be emitted can be uniform in the pixel array APX in consideration of the fact that the radiation is detected after passing through an object (there is an object between the imaging unit 15 and the radiation source 12). Therefore, the pixel array APX may be divided into a plurality of regions, and the monitoring operation MO may be performed for each of the pixels PX in (at least) some of the plurality of divided regions in accordance with the imaging conditions and the like. In other words, in AEC, some of the monitoring results obtained by the monitoring operation MO, which correspond to some of the plurality of divided regions, may be referred to.

Figure 7A:
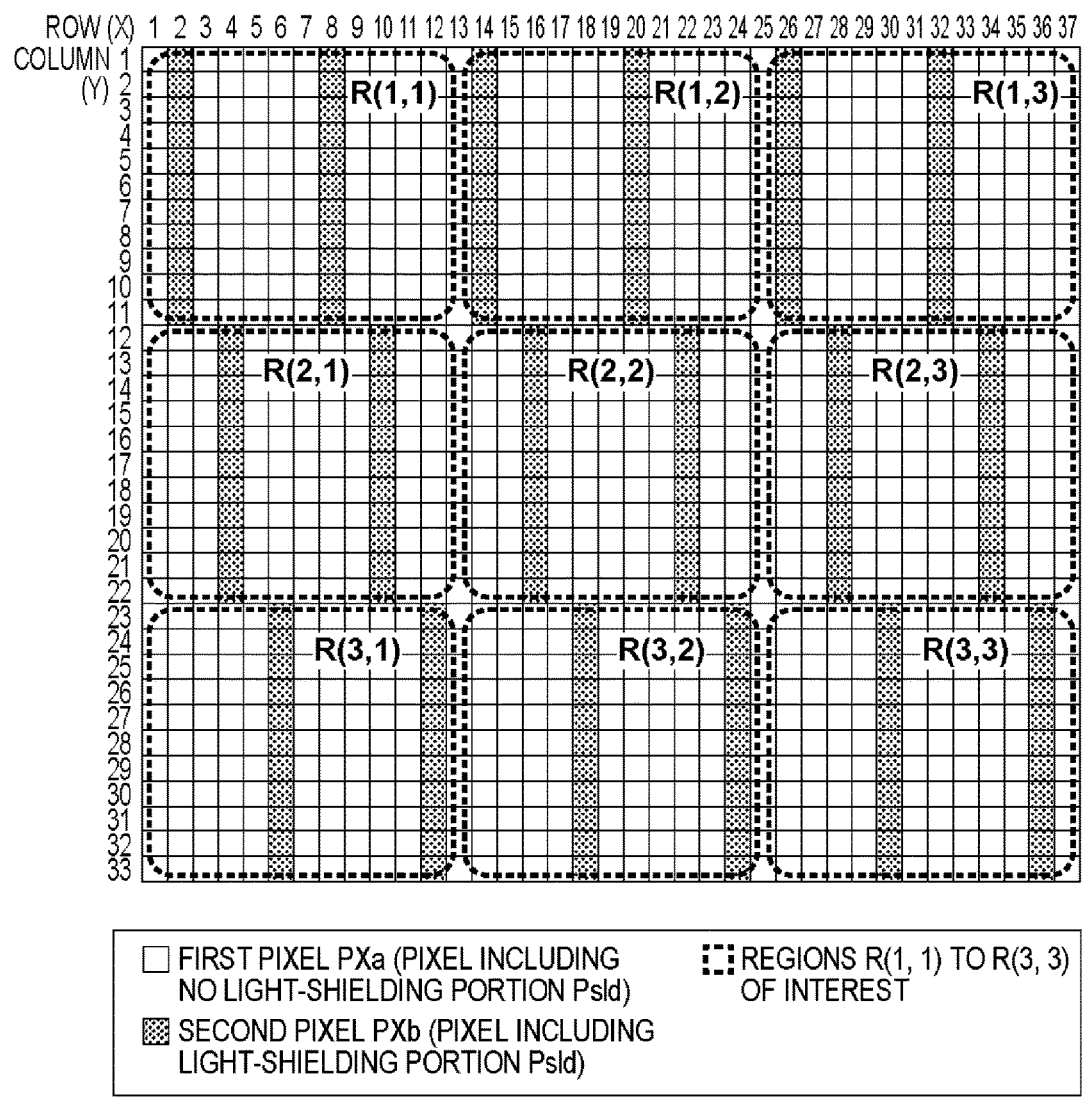
FIG. 7A is a view each for explaining an example of the arrangement of the pixel array.

FIG. 7A shows an example in which the pixel array APX is divided into regions arranged to include three regions in each of the row and column directions (nine regions R(1, 1) to R(3, 3) in total). For the sake of simplicity, in FIG. 7A, a non-hatched pixel indicates the first pixel PXa (a pixel including no light-shielding portion Psld), and a hatched pixel indicates the second pixel PXb (a pixel including the light-shielding portion Psld). As described above, the pixels PXa and PXb are arranged so that the numbers of pixels PXa and PXb are different between adjacent columns. For example, in this embodiment, on an odd-numbered column, the number of pixels PXa is 33 and the number of pixels PXb is 0. On the other hand, on an even-numbered column, the number of pixels PXa is 22 and the number of pixels PXb is 11.

The pixel array APX is divided into the regions R(1, 1) to R(3, 3) so that columns on which the pixels PXb are arranged are different between two adjacent regions in the column direction. For example, the pixels PXb are arranged on the second and eighth columns in the first region R(1, 1), and the pixels PXb are arranged on the fourth and 10th columns in the second region R(2, 1). That is, the columns to which the pixels PXb belong are different between the regions R(1, 1) and R(2, 1).

The monitoring operation MO may be performed for some of the regions R(1, 1) to R(3, 3) in accordance with the imaging conditions and the like. In the above arrangement, the irradiation amount D can be calculated in consideration of weighting of each region. For example, in accordance with the imaging conditions (for example, a portion as an imaging target) input by the user in S401 described above, the monitoring operation MO may be performed for the regions R(1, 1), R(2, 1), and R(3, 1) as end regions of the pixel array APX. In another example, in accordance with the imaging conditions, the weighting coefficient of the given region R(1, 1) or the like may be set larger than that of another region R(1, 2) or the like to perform the monitoring operation MO.

That is, only some of the regions R(1, 1) to R(3, 3), which correspond to the imaging conditions and the like, are referred to. From this viewpoint, each of the regions R(1, 1) to R(3, 3) may be referred to as a "region of interest" hereinafter. Typically, the monitoring operation MO can be performed for a region where radiation is considered to be detected without passing through an object, thereby improving the accuracy of AEC.

Note that to execute such method, part (for example, the readout unit URO) of the arrangement of the imaging unit 15 and/or part of the processing method of the processor 16 may be changed, as needed. For example, in this embodiment, a column line corresponding to each region R(1, 1) or the like may be arranged in the pixel array APX, and the readout unit URO corresponding to each regions R(1, 1) or the like may be provided.

Figure 7B:
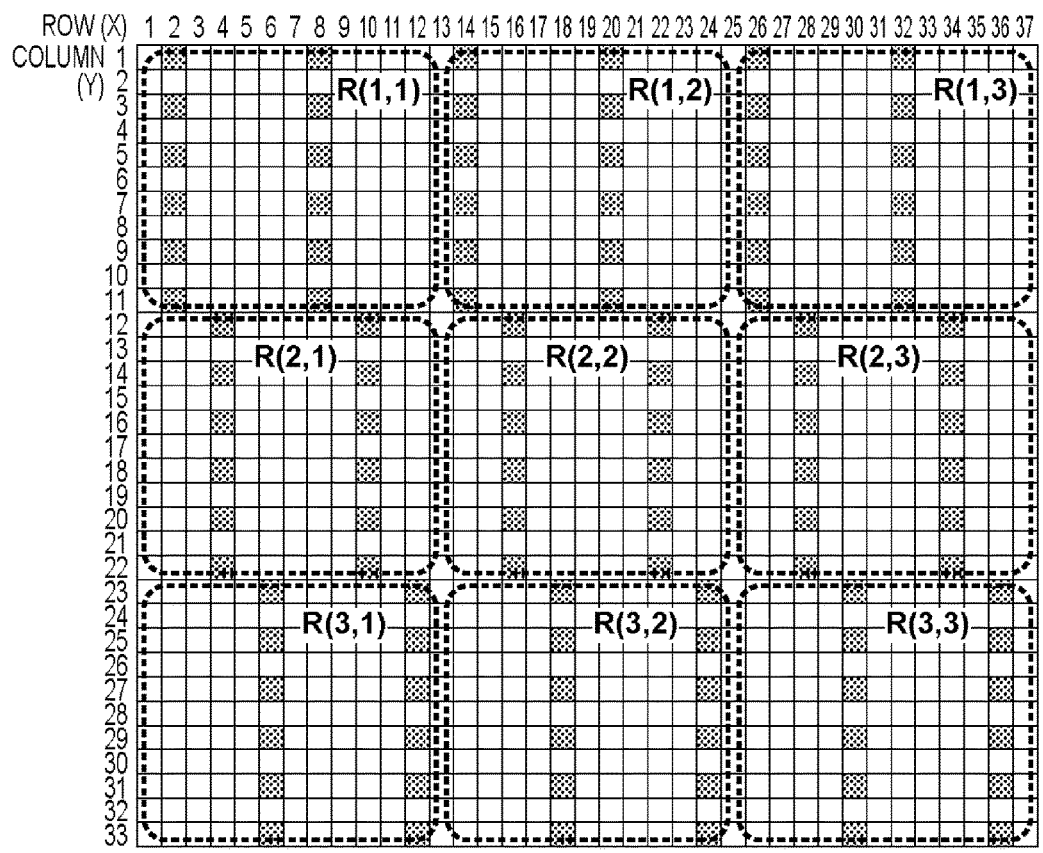
FIG. 7B is a view each for explaining an example of the arrangement of the pixel array.

An example of FIG. 7B is different from the example of FIG. 7A in that in each region R(1, 1) or the like, the pixels PXa and PXb are alternately arranged in the column direction. That is, in the example of FIG. 7B, in each region R(1, 1) or the like, a pixel PXb and another pixel PXb are not adjacent to each other in the column direction. In this arrangement, portions (the pixel signals of the pixels PXb) of the image data obtained by the readout operation RO, which correspond to the pixels PXb, can be corrected or complemented using the pixel signals of the adjacent pixels in the column direction in addition to the pixel signals of the adjacent pixels in the row direction.

Note that a case in which the monitoring operation MO is performed by weighting the monitoring results for two or more regions R(1, 1) and the like has been exemplified. However, the monitoring operation MO may be performed based on the result of another calculation operation, such as the average of the monitoring results, or the difference or ratio between the maximum and minimum values of the monitoring results.

Figure 8A:
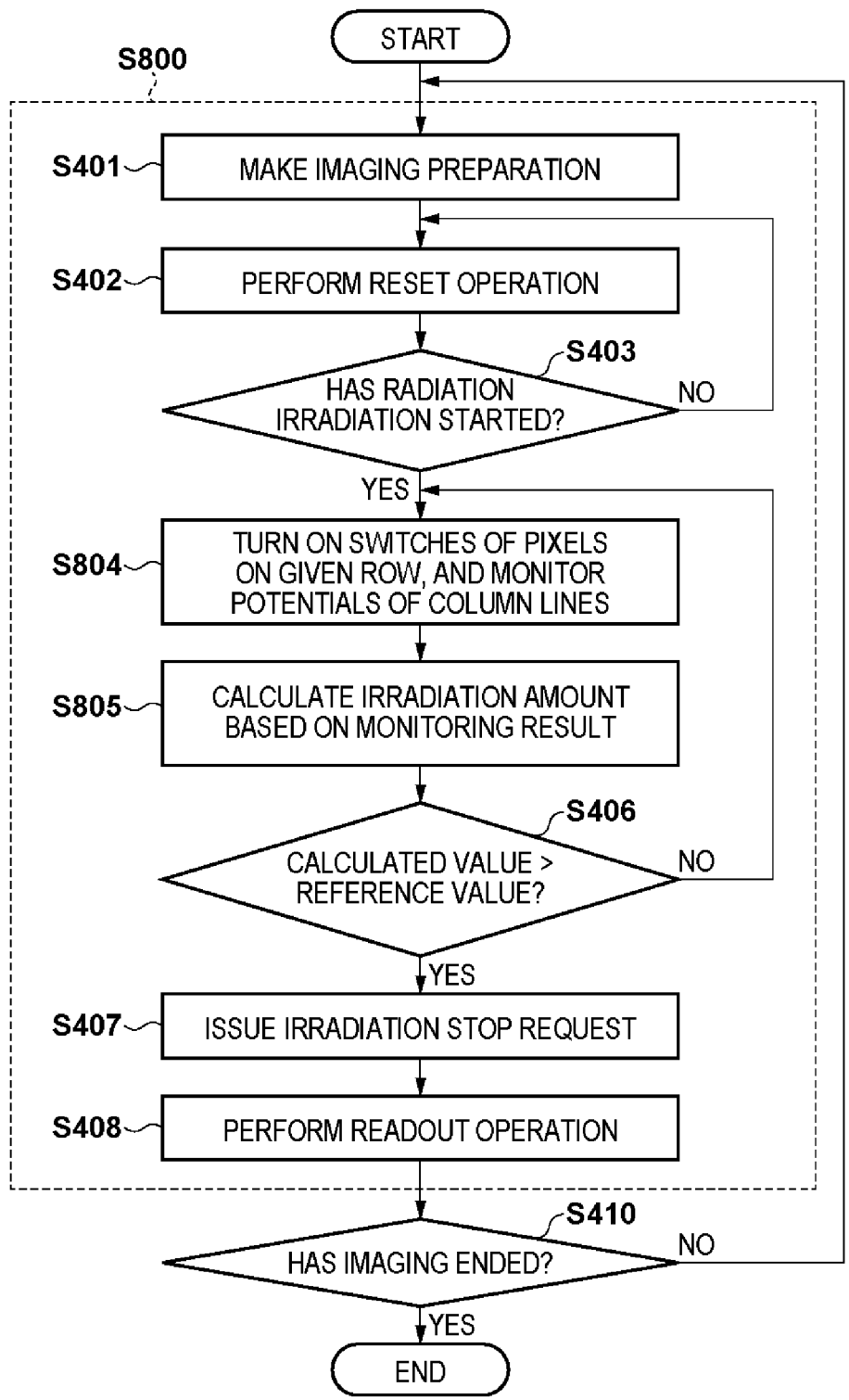
FIG. 8A is an operation flowchart according to a comparative example.
Figure 8B:
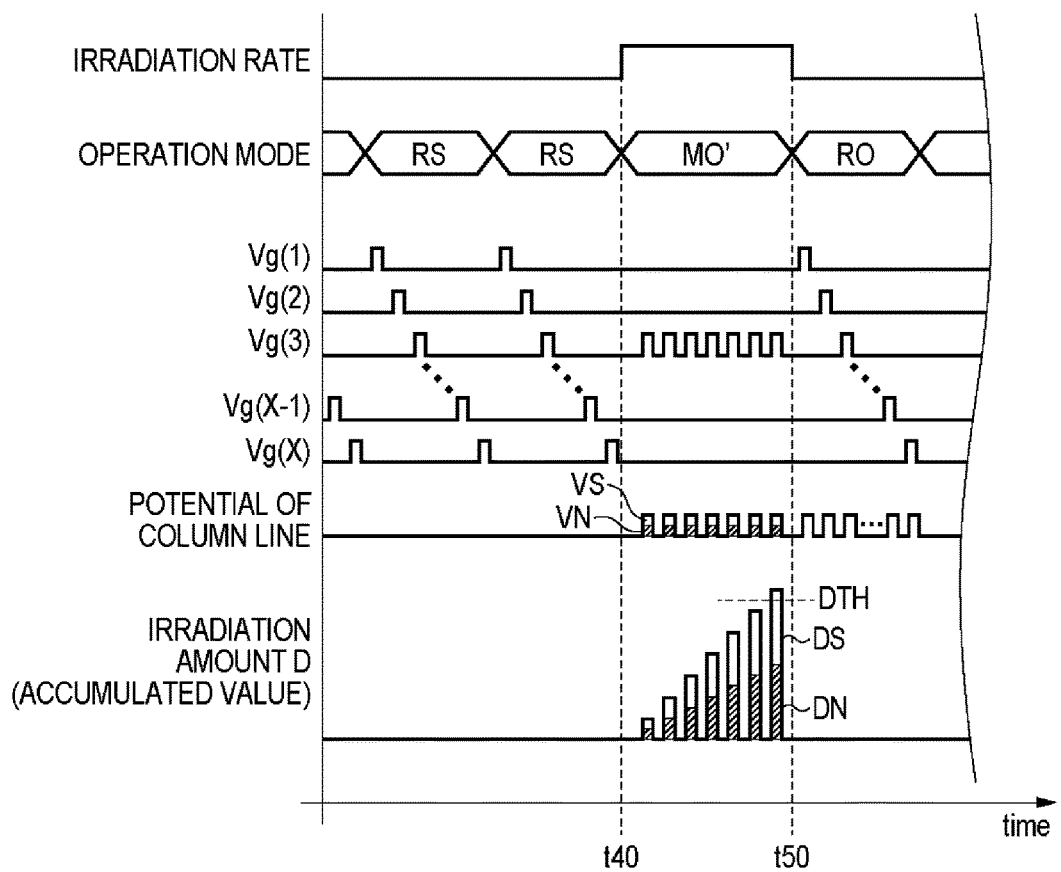
FIG. 8B is an operation timing chart according to a comparative example.

To explain AEC (see FIGS. 4 to 6) in this embodiment and the advantageous effects of AEC in detail, AEC according to a comparative example will be described below with reference to FIGS. 8A and 8B. The comparative example is different from the embodiment of FIGS. 5A and 5B in that only first pixels PXa are arrayed in a pixel array APX (no second pixels PXb are arrayed). FIG. 8A is an operation flowchart according to the comparative example, similarly to FIG. 4 in the embodiment. FIG. 8B is an operation timing chart according to the comparative example, similarly to FIG. 6 in the embodiment.

In the flowchart (FIG. 8A) of the comparative example, a monitoring method in S804 and S805 in S800 in which image data of one frame is acquired is mainly different from the embodiment (FIG. 4). In S804, switches W of pixels PX on a given row are turned on, and signals output to corresponding column lines LC are monitored. Referring to FIG. 8B, a monitoring operation according to the comparative example will be referred to as a "monitoring operation MO'" hereinafter to discriminate it from the monitoring operation MO in the embodiment. As an example, assume that the monitoring operation MO' is performed by turning on the switches W of the pixels PX on the third row (driving a signal line Vg(3)).

In the comparative example, since the switch W is turned on, a component corresponding to an irradiation amount from when radiation irradiation starts until the switch W is turned on or from the previous ON time of the switch W to the next ON time of the switch W is transferred to the corresponding column line LC. The above-described crosstalk is generated in the column line LC together with the component.

The timing chart (FIG. 8B) of the comparative example is mainly different from that (FIG. 6) in the embodiment in that each of the potential of the column line LC and an irradiation amount D includes both a signal component and a crosstalk component. In the comparative example, since the signal component and the crosstalk component are mixed, it is difficult to specify how much amount of the result obtained by the monitoring operation in S804 corresponds to the signal component (or crosstalk component).

For example, in the comparative example, a signal component which can be obtained by turning on the switch W of a given pixel PX is represented by "ES", and a crosstalk component which can be mixed from another pixel PX while the switch W of the other pixel PX is maintained in the OFF state is represented by "EN". In this case, the ratio between the values of these components is, for example, about ES:EN=50:1. However, if the number of pixels in the pixel array APX becomes larger, the value of the crosstalk component EN becomes larger. If, for example, the number of rows of the pixel array APX is 3,000 (a signal component is read out from one pixel PX and crosstalk components are mixed from the remaining 2,999 pixels PX), ES:(2,999×EN) ≈1:60. That is, the signal component (ES) to be originally acquired is buried in the crosstalk components (2,999×EN).

In S805 after S804, the irradiation amount D is calculated based on the results obtained by the monitoring operation in S804. In the comparative example, however, it is difficult to calculate the irradiation amount D with high accuracy for the above reason.

For the sake of simplicity, the signal of the column line LC at the time of the monitoring operation MO' of the comparative example includes the signal component ES and the crosstalk component EN. However, in fact, the signal may also include a noise component caused by an external environment and the like, in addition to the components ES and EN. Assume that in the arrangement (that is, the arrangement in which only the first pixels PXa each including no light-shielding portion Psld are arrayed) of the comparative example, a monitoring operation similar to the monitoring operation MO of the embodiment is performed (that is, a monitoring operation is performed while the switches W of the respective pixels PX are OFF). In this case, in a monitoring result obtained by the monitoring operation, the crosstalk component EN and the noise component are mixed. It is not easy to determine and extract only the crosstalk component EN according to the irradiation amount from the monitoring result. Thus, in the arrangement and monitoring method of the comparative example, it is difficult to calculate the irradiation amount D based on the crosstalk component EN.

To the contrary, in the embodiment, the potentials of the column lines LC are monitored while the switches W of the pixels PX are maintained in the OFF state. It is then possible to acquire the difference between the crosstalk components along with the differences in numbers of pixels PXa and PXb of the two types between adjacent columns while canceling the noise components by calculating the difference between the monitoring results on the adjacent columns. In the embodiment, the irradiation amount D can be appropriately calculated using the difference between the crosstalk components, thereby appropriately determining the timing at which radiation irradiation ends.

For the sake of simplicity, in FIG. 6, each of the irradiation rate and the potential of the column line is constant (the waveform has an ideal rectangular shape) in the monitoring operation MO'. In fact, however, rounding (including ringing) may occur in the waveform due to the setting values of a tube voltage and tube current, the type and state of a tube, and other imaging environments. As in the embodiment, in the indirect conversion type radiation imaging apparatus 11, rounding of the waveform may become conspicuous due to a delay until radiation is converted into light. If the monitoring cycle in the monitoring operation MO' of the comparative example is short, the accuracy of AEC degrades due to rounding of the waveform. On the other hand, if the monitoring cycle in the monitoring operation MO' of the comparative example is increased, a signal component read out by one monitoring operation has a small value, and thus the signal component is buried in noise, resulting in a low S/N ratio. To the contrary, in the embodiment, since a monitoring operation is performed while the switched W of the pixels PX are maintained in the OFF state, even if the monitoring cycle in the monitoring operation MO is increased, no problem that the signal component is buried in noise occurs. Therefore, even if rounding occurs in the waveform, the embodiment is advantageous in improving the accuracy of AEC.

In the monitoring operation MO' of the comparative example, a signal component is read out by turning on the switch W of the pixel PX (so-called destructive readout), and thus part of a pixel signal to be obtained by the readout operation RO thereafter is lost. To the contrary, in the monitoring operation MO of the embodiment, since the switch W of the pixel PX is maintained in the OFF state, no pixel signal is lost. The embodiment is also advantageous in improving the quality of a radiation image.

The present invention is not limited to the embodiment described in this specification, and may partially be changed without departing from the scope of the present invention. Individual terms described in this specification are merely used for the purpose of explaining the present invention. The present invention is not limited to the strict meanings of the terms, as a matter of course, and can also include their equivalents.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-235106, filed Dec. 1, 2015, which is hereby incorporated by reference herein in its entirety.

The invention claimed is:

1. A radiation imaging apparatus including a plurality of pixels which are arrayed to form a plurality of rows and a plurality of columns and each of which includes a detecting element configured to detect radiation and a switch connected to the detecting element, a plurality of column lines respectively corresponding to the plurality of columns and each connected to respective pixels on the corresponding column, and a processor, wherein the plurality of pixels include first pixels and second pixels configured to generate signals of different values by receiving radiation rays of equal irradiation rates, the first pixels and the second pixels are arranged so that the numbers of the first pixels and the second pixels are different between a first column and a second column of the plurality of columns, and the processor performs a first operation of acquiring, as a first signal, a signal of a column line corresponding to the first column and acquiring, as a second signal, a signal of a column line corresponding to the second column while the switch of each pixel is maintained in an OFF state after radiation irradiation for the plurality of pixels starts, a second operation of calculating, based on a discrepancy between the first signal and the second signal, an irradiation amount after the radiation irradiation starts, and a third operation of outputting a signal to end the radiation irradiation in response to a fact that the calculated irradiation amount has reached a reference value.

2. The apparatus according to claim 1, wherein the discrepancy includes at least one of a difference between a signal value of the first signal and a signal value of the second signal, a calculation result corresponding to the difference, a ratio between the signal value of the first signal and the signal value of the second signal, and a calculation result corresponding to the ratio.

3. The apparatus according to claim 1, wherein
the processor calculates the irradiation amount based on the first signal, the second signal, and a predetermined coefficient in the second operation, and
the predetermined coefficient is set based on the number of the first pixels and the number of the second pixels on the first column, and the number of the first pixels and the number of the second pixels on the second column.

4. The apparatus according to claim 1, wherein in the second operation, the processor calculates the irradiation amount based on the number of the first pixels and the number of the second pixels on the first column, and the number of the first pixels and the number of the second pixels on the second column.

5. The apparatus according to claim 1, wherein
each of the first pixels and the second pixels includes a scintillator arranged on a radiation irradiation side, and
if the scintillators receive radiation rays of equal irradiation rates, values of signals generated by the detecting elements of the first pixel and the second pixel are different from each other.

6. The apparatus according to claim 5, wherein
at least one of the first pixel and the second pixel further includes a light-shielding portion, and
the light-shielding portion is arranged so that light beams entering the detecting elements of the first pixel and the second pixel from the scintillators have different light amounts when the scintillators receive radiation rays of equal irradiation rates.

7. The apparatus according to claim 5, wherein sensitivity to light from the scintillator of the detecting element of the first pixel is different from sensitivity to light from the scintillator of the detecting element of the second pixel.

8. The apparatus according to claim 1, wherein a capacitance component of the detecting element of the first pixel is different from a capacitance component of the detecting element of the second pixel.

9. The apparatus according to claim 1, wherein an electrical characteristic of the switch of the first pixel is different from an electrical characteristic of the switch of the second pixel.

10. The apparatus according to claim 1, wherein
the number of the second pixels on the first column is 0, and
the number of the second pixels on the second column is not less than 1.

11. The apparatus according to claim 1, wherein the plurality of pixels are arrayed so that columns on which the second pixels are arranged and columns on which no second pixels are arranged are alternately arranged.

12. The apparatus according to claim 1, wherein the plurality of pixels are arrayed so the second pixels are not adjacent to each other between two adjacent rows.

13. The apparatus according to claim 1, wherein
the plurality of pixels are divided into a plurality of regions in at least a column direction, and
a column on which the second pixels are arranged in a first region of the plurality of regions is different from a column on which the second pixels are arranged in a second region of the plurality of regions.

14. The apparatus according to claim 1, wherein after the third operation, the processor reads out a pixel signal from each of the plurality of pixels by turning on the switch, and performs signal processing for a signal read out from the first pixel and a signal read out from the second pixel by different gains.

15. The apparatus according to claim 1, wherein after the third operation, the processor reads out a pixel signal from each of the plurality of pixels by turning on the switch, and performs one of correction processing and replacement processing of a signal read out from the second pixel using a signal read out from the first pixel adjacent to the second pixel.

16. A radiation imaging apparatus including a plurality of pixels which are arrayed to form a plurality of rows and a plurality of columns and each of which includes a detecting element configured to detect radiation and a switch connected to the detecting element, a plurality of column lines respectively corresponding to the plurality of columns and each connected to respective pixels on the corresponding column, and a processor,
wherein the plurality of pixels include first pixels and second pixels configured to generate signals of different values by receiving radiation rays of equal irradiation rates,
the first pixels and the second pixels are arranged so that the numbers of the first pixels and the second pixels are different between a first column and a second column of the plurality of columns, and
the processor performs
an operation of monitoring a signal generated in a column line corresponding to the first column and a signal generated in a column line corresponding to the second column while the switch of each pixel is maintained in an OFF state after radiation irradiation for the plurality of pixels starts,
an operation of calculating, based on a result of the monitoring, an irradiation amount after the radiation irradiation starts, and
an operation of outputting a signal to end the radiation irradiation in response to a fact that the calculated irradiation amount has reached a reference value.

17. A method of controlling a radiation imaging apparatus including a plurality of pixels which are arrayed to form a plurality of rows and a plurality of columns and each of which includes a detecting element configured to detect radiation and a switch connected to the detecting element, and a plurality of column lines respectively corresponding to the plurality of columns and each connected to respective pixels on the corresponding column,
the plurality of pixels including first pixels and second pixels configured to generate signals of different values by receiving radiation rays of equal irradiation rates, and
the first pixels and the second pixels being arranged so that the numbers of the first pixels and the second pixels are different between a first column and a second column of the plurality of columns,
the method comprising
acquiring, as a first signal, a signal of a column line corresponding to the first column and acquiring, as a second signal, a signal of a column line corresponding to the second column while the switch of each pixel is maintained in an OFF state after radiation irradiation for the plurality of pixels starts,
calculating, based on a discrepancy between the first signal and the second signal, an irradiation amount after the radiation irradiation starts, and
outputting a signal to end the radiation irradiation in response to a fact that the calculated irradiation amount has reached a reference value.

* * * * *